United States Patent

Albrecht et al.

[11] Patent Number: 5,954,677
[45] Date of Patent: Sep. 21, 1999

[54] DEVICE FOR THE REDUCTION OF A DEFICIT IN EXTENSION OR BENDING OF A DISTAL MEMBER OF THE BODY IN RELATION TO A PROXIMAL MEMBER

[75] Inventors: Erich Albrecht; Hans Georg Opahle, both of Rosenheim, Germany

[73] Assignee: Albrecht GmbH, Stephanskirchen, Germany

[21] Appl. No.: 08/962,275

[22] Filed: Oct. 31, 1997

[30] Foreign Application Priority Data

Oct. 31, 1996 [DE] Germany .............................. 196 45 076

[51] Int. Cl.[6] .................................................. A61F 5/00
[52] U.S. Cl. ................................................. 602/16; 602/26
[58] Field of Search ..................... 602/5, 16, 20, 602/23, 26

[56] References Cited

U.S. PATENT DOCUMENTS

| | | |
|---|---|---|
| 4,686,969 | 8/1987 | Scott . |
| 5,036,837 | 8/1991 | Mitchell et al. ................. 602/16 X |
| 5,399,149 | 3/1995 | Frankowiak et al. ................. 602/16 |
| 5,399,154 | 3/1995 | Kipnis et al. . |
| 5,409,449 | 4/1995 | Nebolon ........................... 602/16 |
| 5,437,611 | 8/1995 | Stern . |
| 5,520,627 | 5/1996 | Malewicz . |
| 5,624,390 | 4/1997 | Van Dyne ........................... 602/16 |
| 5,672,152 | 9/1997 | Mason et al. ..................... 602/16 X |

FOREIGN PATENT DOCUMENTS

PS 387 585   1/1924   Germany .

*Primary Examiner*—Linda C.M. Dvorak
*Attorney, Agent, or Firm*—Nixon & Vanderhye

[57] ABSTRACT

In the case of a device for reducing deficits in extension or bending of a distal body member in relation to an adjacent proximal body member articulating with the distal body member a spring force locking mechanism (28, 29 and 31) is provided, which is able to be pivoted between a non-locking state, wherein the biasing force of the spring (34) is able to be freely transmitted to the distal splint (1), and a locking state, wherein the biasing force of the spring (34) is de-coupled from the distal splint (1) and is taken up by the spring force locking mechanism (28, 29 and 31) so that the distal splint (1) is able to be pivoted without any spring action over the free pivoting range.

11 Claims, 5 Drawing Sheets

DEVICE FOR THE REDUCTION OF A DEFICIT IN EXTENSION OR BENDING OF A DISTAL MEMBER OF THE BODY IN RELATION TO A PROXIMAL MEMBER

BACKGROUND OF THE INVENTION

The invention relates to a device for the reduction of a deficit in extension or bending of a distal member of the body in relation to an adjacent proximal member of the body articulatingly connected with the distal body member.

It is more particularly joint capsules and/or connective tissues which frequently suffer from a deficit in extension or bending following a ligament operation, an accident, inflammation etc. This means that a distal member of the body, as for example the lower leg, can no longer be completely moved into its normal position of extension or flexion in relation to a proximal body member, as for instance the upper leg.

In order to counter-act such a deficit in extension or bending it is a known practice to stretch the shrunk tissues by using a so-called brace device to set the distal body member in relation to the proximal body member in a certain braced position or to use spring force to urge same into this braced position.

In the case of known knee orthoses setting of the trochoid in the braced position is performed using screws or pins, which may be introduced into corresponding transverse holes. It is a disadvantage with such known knee orthoses that a patient with a set or fixed trochoid joint is not able to walk or can only do so with great difficulty, since the knee can not be flexed. Furthermore the removal and, respectively, insertion of the locking pins or screws involves time and effort. It is particularly significant that the setting of the upper and lower leg in the braced position frequently gives rise to pain after only a short time so that the braced position may only be maintained for a short time. The success of this method for compensation of an extension or bending deficit consequently leaves much to be desired.

Furthermore a bracing device has been proposed, in the case of which the distal splint is permanently urged into the desired bracing direction by means of spring bias. It is however more particularly a disadvantage here that such a bracing device must as a rule be removed every time the joint is to be moved in the direction opposite to the bracing direction, for instance in order, after the occurrence of pain, to relieve ligaments, to perform investigations or to be able to move the respective members of the body normally. If such a known bracing device is not taken off, the last mentioned activities are usually not possible at all or only possible to a restricted extent.

SUMMARY OF THE INVENTION

One object of the invention is to provide a device with which on the one hand an extension or bending deficit of a distal body member in relation to a proximal body member may be dealt with in the simplest and most effective way and on the other hand furthermore the patient is offered a greater possibility of movement and greater comfort when wearing the device.

In the device of the invention a spring force locking mechanism is provided that is able to be changed over between a non-locking condition, wherein the biasing force of the spring is able to be freely transmitted to the distal splint and a locking condition, wherein the biasing force of the spring is de-coupled from the distal splint and is taken up by the spring force locking mechanism so that the distal splint is able to be pivoted, without any spring action, along the free pivoting range.

In the case of the joint support of the invention the spring exerts a continuously acting biasing force on the distal splint so that same is permanently drawn or thrust into the desired bracing direction as far as a terminal abutment, which sets the maximum permitted extension or flexion. The position of this terminal abutment may be preferably changed in accordance with desired maximum extension range. It is particularly advantageous if the position of the terminal abutment is able to be steplessly adjusted or set, at least within a certain angular range, since then the limit of the pivotal range and accordingly the range of bracing may be adapted with great precision to the degree of extension or bending of the patient applying and they may be accordingly re-set (Controlled Passive Stretching or CPS). The spring force sets the torque with which the distal splint is turned in relation to the proximal splint. Despite the biasing force of the spring the patient still has the possibility of flexing the joint in case of need. With the aid of the spring force locking mechanism of the invention it is namely possible to completely uncouple the biasing force of the spring from the distal splint. The distal splint may in this case be moved completely freely out of any flexed position as far as the maximum extension or flexion position. Simply by resetting the spring force locking mechanism the patient is able to select between a stretching or bending biasing action and free mobility of the joint. In this respect it is a particular advantage that even with the spring force disconnected, the setting for the degree biasing force is maintained.

It is preferred for the spring to be a spiral spring surrounding the pivot axis pin, one end being operatively connected with the one splint and the other end is connected, in the end state of the spiral spring, with the other splint. It is in this manner that it is possible to provide a particularly compact design which at the same time ensures a strong spring force.

It is convenient for a biasing force modifying device to be provided, which is operatively connected with one end of the spring and in the case of which the relative position of such spring end in relation to the other spring end may be modified. This biasing force modifying device is particularly advantageous, since an individual adaptation of the spring biasing force to the requirements of the patient is rendered possible and the distal body member and can drawn or thrust with an optimized extending or bending force in the extension or, respectively, flexion direction.

In accordance with an advantageous embodiment the biasing force modifying device comprises a gear wheel able to be turned about the pivot axis and able to be set by means of a gear wheel locking mechanism in relation to one splint, one end of the spring being secured in a portion adjacent to the axis of rotation. The biasing force of the spring may in this manner be modified in a simple manner by turning and locking of the gear wheel in a new position.

In order to perform this manual rotation of such gear wheel, for example using a screw driver, even when subject to a great spring force, it is an advantage, if a further actuating gear wheel is in mesh with the gear wheel, such further gear wheel having a smaller diameter, in order to constitute a gearing transmission.

It is an advantage if the spring force locking mechanism comprises a coupling element arranged between the spring and the distal splint, such coupling element being on the one hand connected with one end of the spring and on the other hand being able to be brought into engagement with the distal splint. In its unlocked state the coupling element then urges the distal splint, owing to the biasing force of the spring, permanently in the desired direction of rotation, whereas in its locked state it is prevented from moving in this direction of rotation. This means that, when the coupling element is locked, the distal splint is able to move completely freely, that is to say is uncoupled from the spring force, in the remaining range of pivoting as far as the terminal abutment for extension or flexion, if for example the patient desires to move the joint normally or if the mobility of the joint is to be investigated without any effect on the spring force.

Such locking of the spring force may be produced in an extremely simple manner, if the coupling element has radially inwardly extending recesses in its outer periphery, into which recesses a locking pin slidingly held on the proximal splint may be introduced. This locking pin is conveniently so designed that it projects outwardly and may be grasped and actuated by the patient or a physician in a simple manner.

BRIEF DESCRIPTION OF THE DRAWING FIGURES

The invention will now be explained with reference to the drawings in detail.

DESCRIPTION OF THE PREFERRED EMBODIMENT

Figure 1:
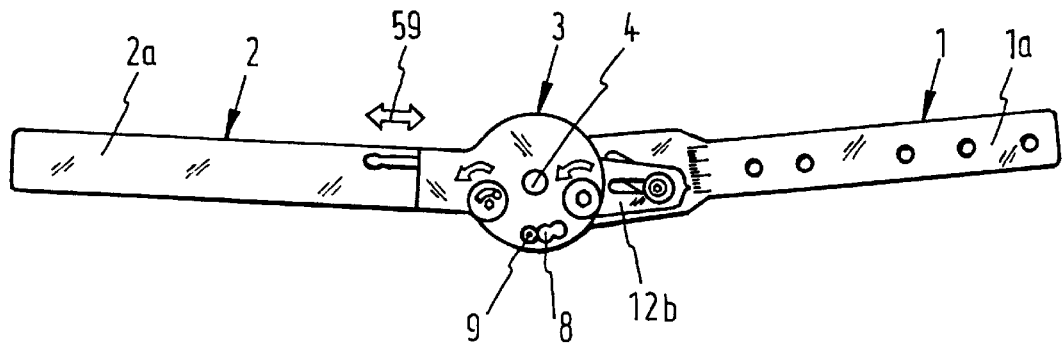
FIG. 1 is a plan view of the device of the invention.
Figure 2:
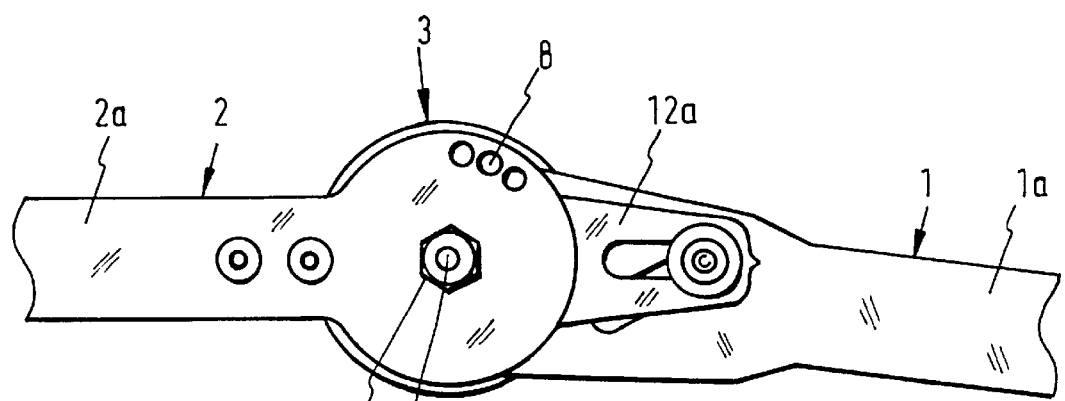
FIG. 2 is a view from below of the device of FIG. 1 in a somewhat greater scale, the free portions of the splints being shown cut away.

In the following the device of the invention will be described with reference to FIGS. 1 through 8, two devices being regularly employed which are placed on opposite sides of the joint. The device to be arranged on the opposite side of the joint is designed symmetrically. Attachment straps for the attachment of the proximal and distal splints on the proximal and, respectively, distal body member are omitted in order to make the drawing more straightforward. The device in accordance with the invention will be described with reference to an embodiment of a bracing device for a knee, although it may be employed for other joints, as for example the elbow joint.

Figure 7:
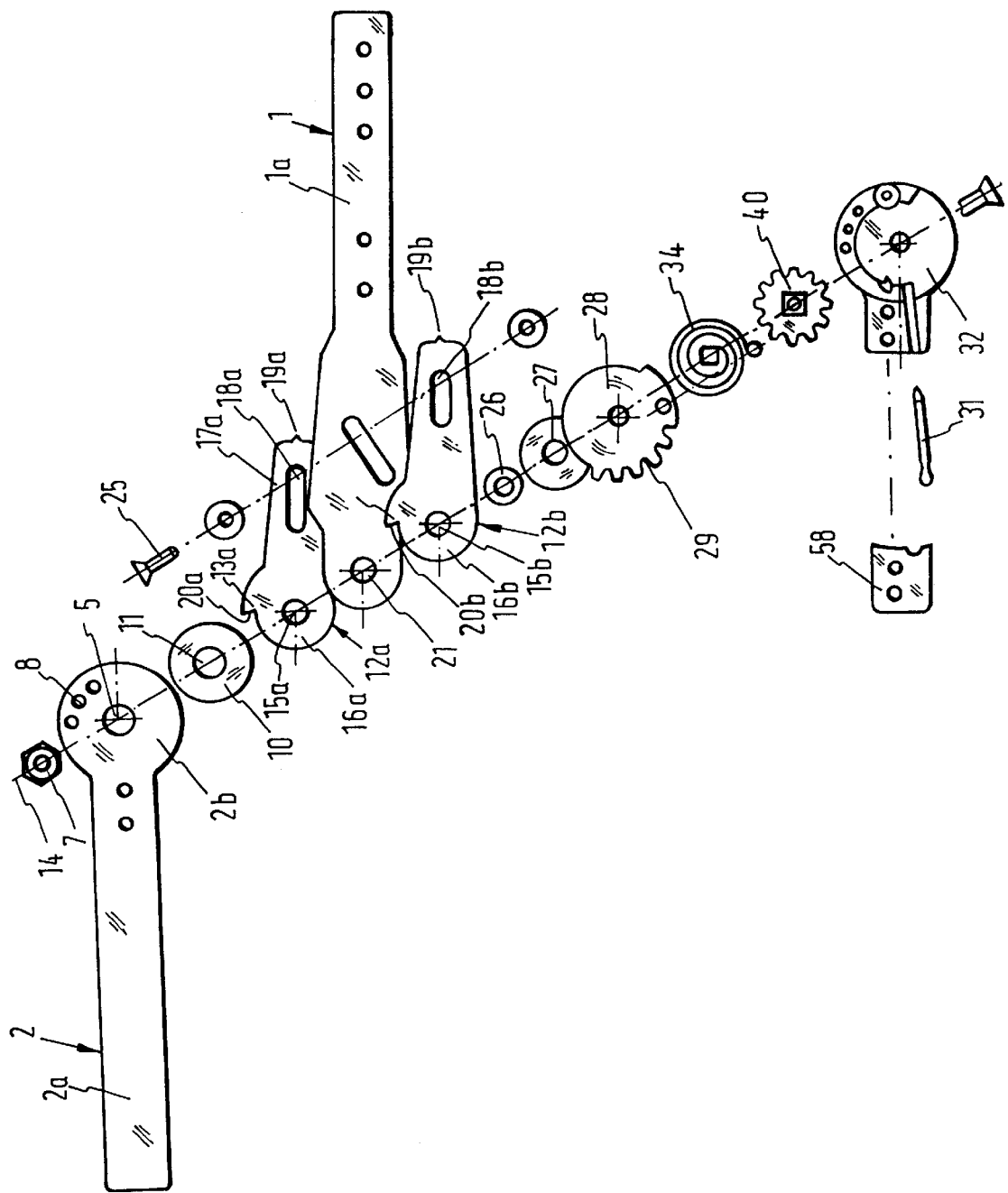
FIG. 7 is an exploded view of the entire device without the attachment straps.

As shown in FIG. 1 and the exploded view of FIG. 7, the device of the invention comprises a distal splint 1 with an attachment section 1a, which by the intermediary of suitable straps, not illustrated, may be secured to the lower leg, and a proximal splint 2 with an attachment section 2a, which may also be secured by means of suitable straps, not illustrated either, to the upper leg and by means of a pivot joint 3 articulates with the distal splint 1. The pivot axis pin is here referenced 14.

Figure 3:
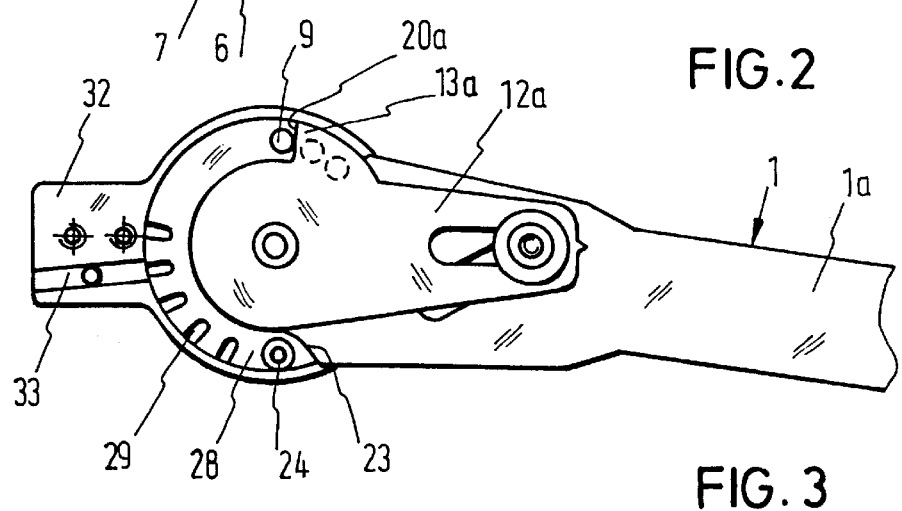
FIG. 3 shows a view from below in accordance with FIG. 2, the proximal splint and a spacing member having been removed.
Figure 4:
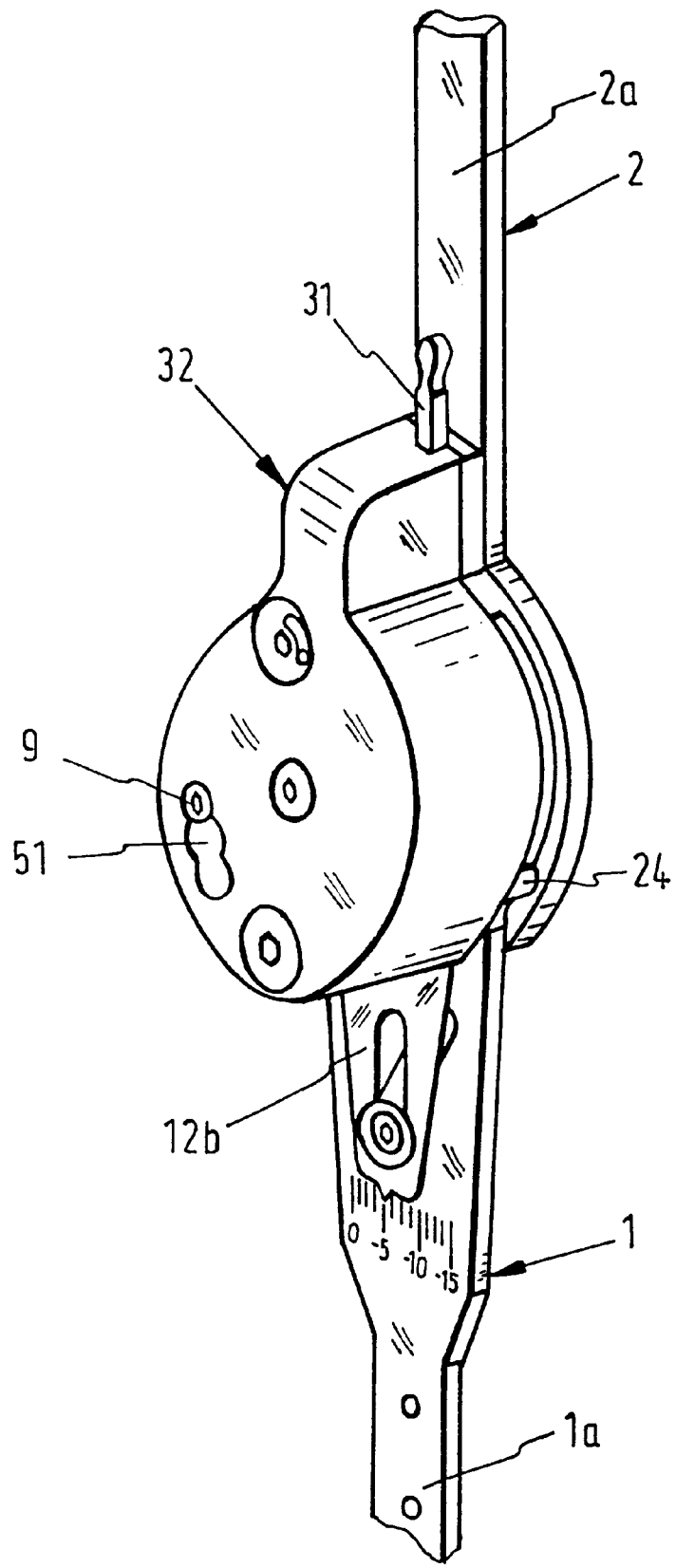
FIG. 4 is a perspective view of the device in accordance with the invention, the free ends of the proximal and distal splints having been cut away.
Figure 5:
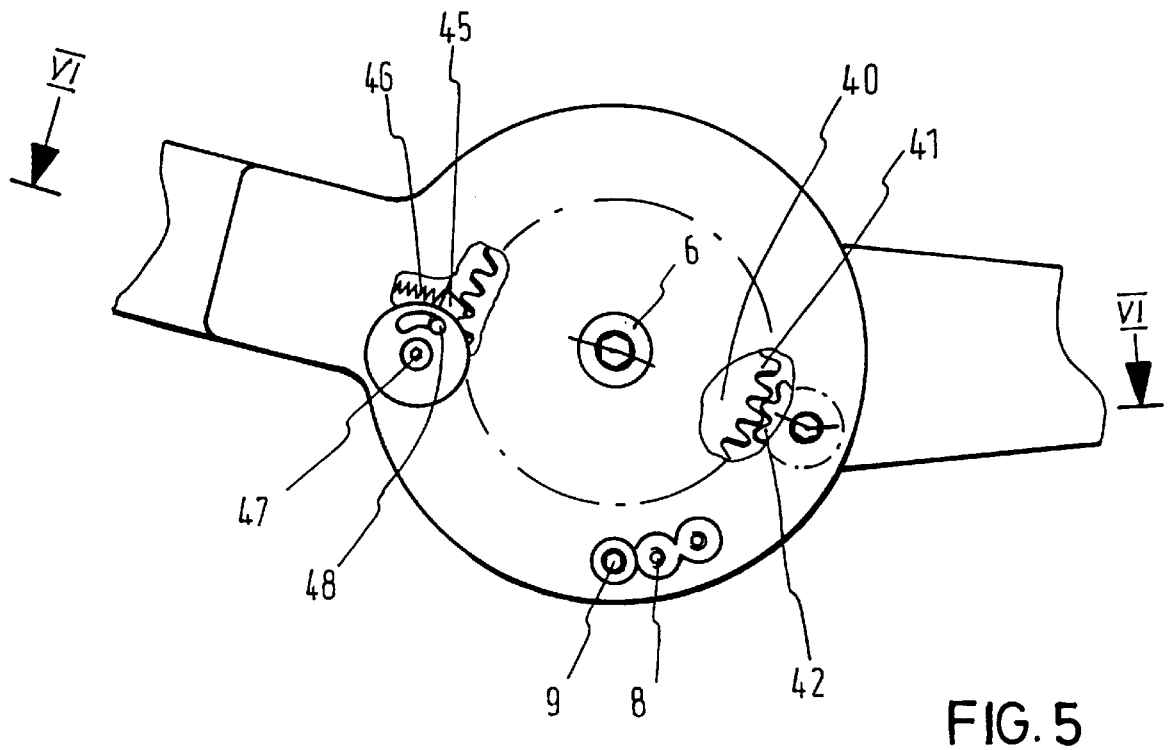
FIG. 5 is a plan view of the middle part of the device, some parts having been cut away in order to indicate the biasing force modifying device and the gear wheel locking mechanism.

As apparent from FIG. 7 a joint section 2b in the form of a circular disk of the proximal splint 2 has a hole 5 in its center for the insertion therethrough of a joint pin 6 which is only indicated diagrammatically, which on the opposite side of the proximal splint 2 may be secured with the aid of a nut 7. In the vicinity of the outer periphery of the joint section 2b three extension limiting holes 8 are also provided as shown in FIGS. 3, 4 and 5, which are arranged in the peripheral direction on after the other and serve to receive an extension limiting pin 9 designed in the form of a screw. Two adjacent extension limiting holes 8 are respectively offset from one another in the peripheral direction by an angle of 15°.

The proximal splint 2 constitutes that inner part of the device which is farthest to the side and which accordingly, provided with a suitable pad and/or suitable shell part adapted to the upper leg, engages the upper leg of the patient.

As furthermore shown in FIG. 7, the joint section 2b of the proximal splint 2 is adjoined on the outside by a circular friction reducing disk or washer 10, which for example may consist of a thin plastic sheet. The friction reducing disk 10 possesses a central through opening 11 for the passage of a joint pin 6.

In the outward direction there then follows one half of an angle setting element 12, which engages the inner side of the distal splint 1 and, with the possibility of relative movement about the pivot axis pin 14, engages the splint 1. The other half 12b is identical to the half 12a and engages the opposite side of the distal splint 1 with a possibility of relative movement. Both halves 12a and 12b possess radially projecting spurs 13a and 13b, which together constitute a bridge portion since they are connected with one another.

Each angle setting element half 18a and 18b comprises a thin but strong sheet metal component and is mounted for pivotal movement about the pivot axis pin 14, such pivot axis being the common axis for all joint support parts. For this purpose the halves 12a and 12b possess a through hole 15a and 15b, through which the joint pin 6 may be inserted. The proximal end of the halves 12a and 12b is designed in the form of a semicircular section 16a and 16b, the radius of such semicircle being smaller than the radius of the circular arc, on which the extension limiting holes 8 in the proximal splint 2 are placed. These holes 8 are accordingly not covered over by the semicircular section 16a and 16b of the angle setting element halves 18a and 18b. It is convenient for the radius of the semicircular section 16a and 16b to be the same as that of the friction reducing disk 10.

The semicircular section 16a and 16b of the angle setting element halves 12a and 12b is adjoined by an elongated handle section 17a and 17b, in which a slot 18a and 18b is located, such slots being aligned with the longitudinal direction of the angle setting element halves 12a and 12b. At the distal end of the handle section 17a and 17b there is a pointer 19a and 19b.

The previously mentioned spurs 13a and 13b of the angle setting element halves 12 and 12b extend in the radial direction past the extension limiting holes 8 to the outside so that an end contact surface 20a and 20b of the spurs 13a and 13b may engage the extension limiting pin 9 (FIG. 3), which pin represents an abutment element attached to the proximal end splint 2 for limiting extension.

As furthermore indicated in FIG. 7 the distal splint 1 possesses a through opening 21 for the insertion of the joint pin 6, the arc extending for somewhat more than 180°, as for example 220°. The radius of this semicircular section again corresponds to that of the semicircular section 16a and 16b of the angle setting element halves 12a and 12b. Following the essentially semicircular section the distal splint 1 becomes wider so that an end abutment surface 23 is formed for an entrainment pin 24 (FIGS. 3 and 8) to be described later herein.

As shown in FIG. 7 the distal splint 1 furthermore possesses an obliquely arranged slot 22, whose longitudinal axis makes an angle of 34° with the longitudinal axis of the distal splint 1 in the present embodiment of the invention. The slot 22 in the distal splint 1 consequently extends obliquely in relation to the slots 18a and 18b in the angle setting element halves 12a and 12b, the slots 22; 18a and 18b overlapping.

Owing to the indicated arrangement of the slots 22; 18a and 18b the angular position of the angle setting element halves 12a and 12b may be steplessly set, and with them the limit of extension, in relation to the distal splint 1, by a displacement of a stop screw 25, inserted through the slots 22; 18a and 18b, along the slots 22; 18a and 18b.

As furthermore apparent from FIGS. 6 and 7 a relatively small bushing 26 having an internal screw thread is able to be screwed on a corresponding threaded section of the joint pin 6 in order on the one hand to hold together parts of the device which are later to be described, and on the other hand to serve as a rotary bearing for the distal splint 1 and the angle setting element halves 12a and 12b.

On the outside of the outer angle setting element half 12 there adjoins a further friction reducing disk 27, which is designed in the same manner as the friction reducing disk 10.

Figure 8:
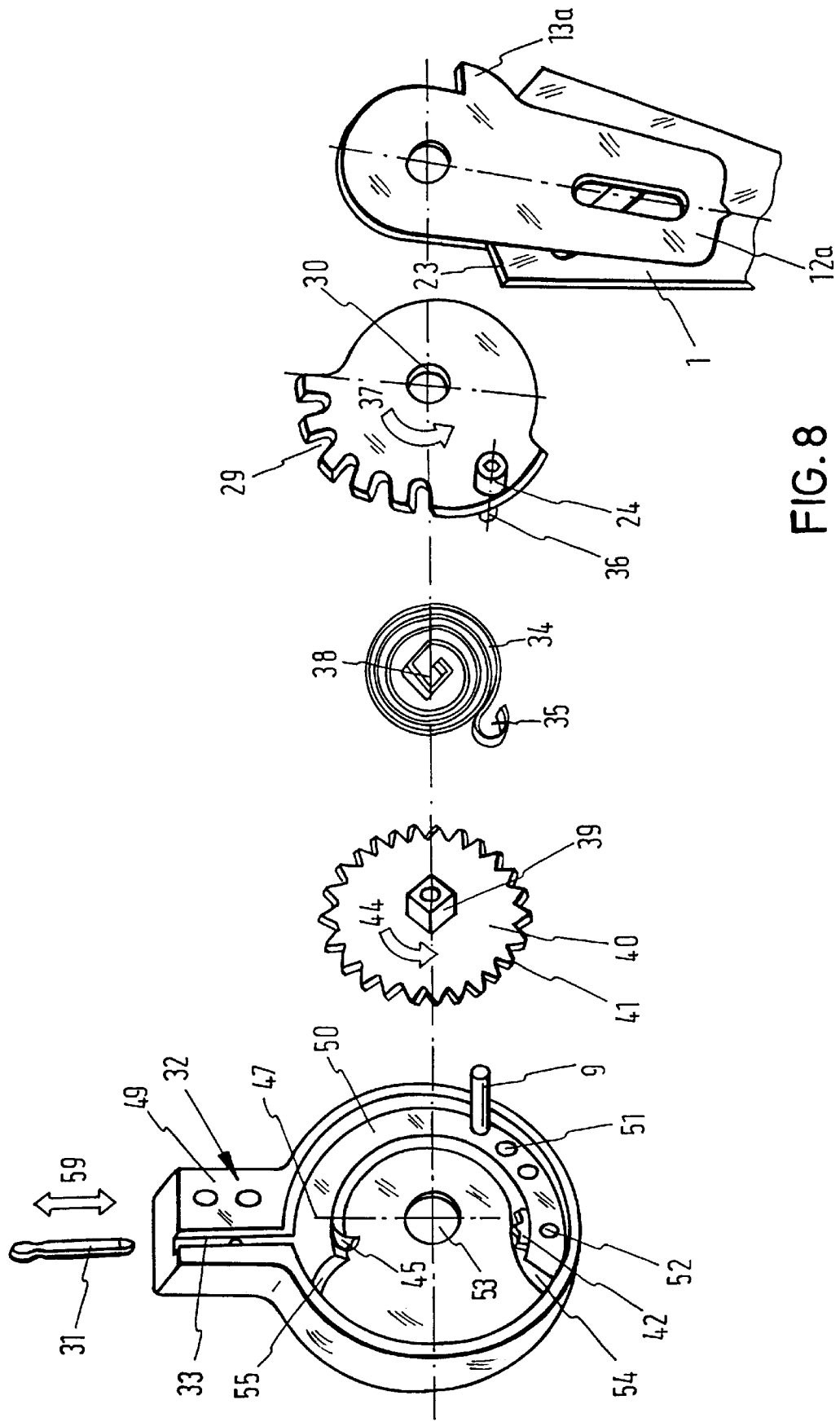
FIG. 8 is a perspectively drawn exploded view of the main parts in order to indicate the transmission and, respectively, locking of spring forces between the proximal and the distal splint.

The friction reducing disk 27 is adjoined by a disk-like coupling element 28, which is illustrated in more detail in FIG. 8. On somewhat more than half of its outer periphery, as for example 205°, this coupling element 28 has a radius which is smaller than the rest of the outer periphery, which possesses a plurality of adjacently placed and radially inwardly extending recesses 29. In this last named peripheral section the coupling element 28 is accordingly designed like a spur gear wheel. In this part the already mentioned entrainment pin 24 (see FIGS. 3 and 8) with a larger diameter is also attached to the coupling element 28 and projects in parallelism to the pivot axis pin past the side surface of the coupling element 28. The joint pin 6 illustrated in FIG. 7 may be inserted through a central through hole 30 in the coupling element 28.

In the recess 29 a stop pin 31 may be inserted to prevent rotary movement of the coupling element 28, such stop pin being held on a proximal rotary joint housing 32 within a groove 33 to permit longitudinal sliding motion (FIG. 8).

A spring 34 in the form of a spiral spring laterally adjoins the coupling element 28. The outer free end of the spring 34 is designed in the form of a coupling eye 35, into which an entrainment pin 36, attached to the coupling element 28, may be inserted. This entrainment pin 36 projects past the coupling element 28 in the opposite direction to the entrainment pin 24. It is convenient for both entrainment pins 24 and 36 to be formed by a single allen screw, which is so screwed through a corresponding threaded hole in the coupling element 28 that the threaded shank projects on the other side of the coupling elements 28.

In the assembled state the spring 34 exerts a constant biasing or bracing force on the coupling element 28 so that the force tends to turn the coupling element in the direction of the arrow 37.

The inner free end of the spring 34 is wound up to define the shape of a central square through hole 38 so that the spring 34 may be slipped over a corresponding square central holding pin 39 of a gear wheel 40 in such a manner as to prevent relative rotation. The gear wheel 40 possesses spur teeth 41, which mesh with corresponding teeth on a substantially smaller actuating gear wheel 42 (FIGS. 5 and 6). This actuating gear wheel 42 is mounted for rotation in a part of the rotary joint housing 32 near the outer periphery and may be turned through a corresponding opening 43 in the rotary joint housing 32 from the outside, as for example using an allen screw wrench.

Together with the gear wheel 40 the actuating gear wheel 42 constitutes transmission gearing in order, using the holding pin 39, to wind up the spring 34 using its inner end in the direction of the arrow 44 and consequently to increase the biasing force.

In order, after adjustment of the desired biasing force, to ensure that the gear wheel remains in the desired position and is not turned back oppositely to the direction of the arrow 44, the rotary joint housing 32 has a gear wheel locking means in the form of a locking ratchet 45 pivotally mounted in it. The locking ratchet pawl 45 is designed in the form of a pivoting lever and owing to the driving force of a ratchet pawl spring 46 (FIG. 5) engages the spur gear teeth 41 of the gear wheel 40. The pivot axis pin for the ratchet pawl is referenced 47 in FIG. 5. Furthermore an actuating pin 48 is provided on the ratchet pawl 45, such pin 48 being able to be actuated from the outside through a suitable opening in the housing 32 of the rotary joint in order to move the ratchet pawl 45 against the force of the ratchet pawl spring 46 out of engagement with the gear wheel 40.

As shown in FIG. 8 the rotary joint housing 32, which is fixedly connected with the proximal splint 2, not illustrated in FIG. 8, is essentially designed in the form of a circular pan, having a laterally projecting, solid attachment lug 49 for attachment of the proximal splint 2. From the lateral inner wall of the circular pan a solid rib 50 extends radially inwardly, such rib occupying an angle of approximately 250° in the peripheral direction and running out from the portion with the attachment lug 49. In such rib 50 there are three extension limiting through holes 51 arranged adjacent to each other in the peripheral direction, such holes being exactly opposite to the extension limiting holes 8 in the proximal splint 2 (FIGS. 2 and 7) and serving for screwing in the extension limiting pin 9. The pivot axis pin 52 for the actuating gear wheel 42 and the pivot axis pin 47 for the ratchet pawl 45 are also rotatably mounted in the rib 50.

Figure 6:
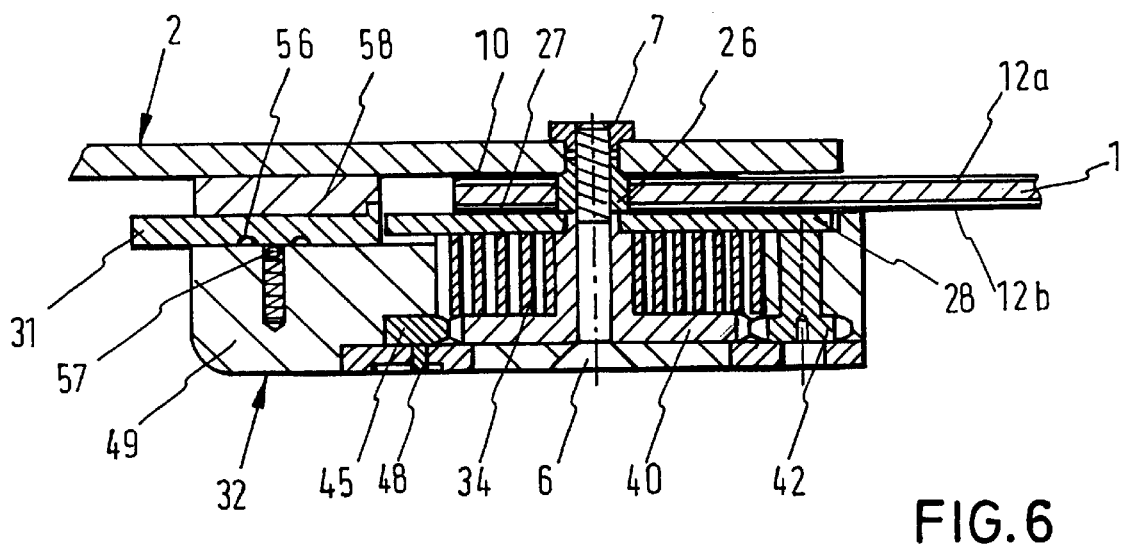
FIG. 6 shows a vertical section taken along the line VI—VI of FIG. 5.

The sunken portion radially within the rib 50, i. e. the portion about a central through hole 53, serves to receive the gear wheel 40 and the spring slipped 34 on it as will be apparent from the vertical section of FIG. 6. The projecting free outer end of the spring 34 with the eye 35 and the entrainment pin 36 received therein of the coupling element 28 are in the present case in the portion, near to the side, within the rotary joint housing 32, over which the rib 50 does not extend, that is to say in the portion between the end walls 54 and 55 of the rib 50. In the maximum permissible extension setting of the distal splint 1, which is illustrated in FIG. 8, the eye 35 of the spring 34 is near the end wall 54.

If the knee is bent, i. e. moved in the flexion direction, the eye 35 of the spring 34 will move toward the opposite end wall 55 of the rib 50.

From FIG. 6 it will furthermore be apparent that the stop pin 31 placed in the groove 33 has notches 56 in its lower surface in order to hold the stop pin 31 in its end positions after thrusting in an spring-loaded detent ball inward.

As furthermore indicated in FIG. 6, between the attachment lug 49 of the rotary joint housing 32 and the proximal splint 2 a spacing member 58 is provided in order to maintain a sufficient clearance between the proximal splint and the coupling element 28 to receive the proximal splint 1. The proximal splint 2 is fixedly screwed to the attachment lug 49 through the spacing member 58.

The manner of operation of the joint support as illustrated will now be explained with reference to FIG. 8.

In the normal state the spring 34, which by means of its inner end on the holding pin 39 of the gear wheel 40 is held within the rotary joint housing 32, urges—by means of the entrainment pin 36—the coupling element 28 to perform a rotary movement in the direction of the arrow 37, FIG. 8 already showing the maximum possible pivot position in this direction. However a condition for this is that the tip of the stop pin 31 does not extend into the pan-like part of the rotary joint housing 32 and therefore into one of the recesses 29 in the coupling element 28, and is so far drawn back that the pivot movement of the coupling element 28 is not impeded. In this condition the entrainment pin 24 of the coupling part 28 is in constant engagement with the abutment surface 23 of the distal splint 1 so that a torque in the clockwise direction, i. e. in the extension direction, is constantly applied to the splint 1. This pivotal movement lasts until the spurs 13a and 13b of the angle setting element 12 strike against the extension limiting pin 9, which extends through the entire rotary joint. Simultaneously however pivotal movement of the distal splint 1 in relation to the rotary joint housing 32 and hence in relation to the proximal splint 2 is possible in the clockwise direction, i. e. in the direction of flexion, the biasing force of the spring 34 having to be overcome.

If the biasing force of the spring 34 on the distal splint 1 is to be discontinued, the distal splint 1 is firstly pivoted in the flexion direction, that is to say in the clockwise direction in terms of FIG. 8, until one of the recesses 29 in the coupling element 28 is aligned with the stop pin 31 and the latter may be inserted into the corresponding recess 29. This displacement of the stop pin 31 is indicated by a double arrow 59 in FIGS. 1 and 8. Once the further pivotal movement of the coupling element 28 is locked in this manner, the distal splint 1 may be released from the entrainment pin 24 and move freely as far as the maximum position of extension. It will be apparent that the pivotal range free of biasing force of the distal splint becomes larger as the splint is moved back in the flexion direction before the insertion of the stop pin 31. If the stop pin 31 is inserted in that recess 29 in the coupling element 28 which is nearest to the entrainment pins 24 and 36, the pivotal range of the distal splint 1 which is free of spring force will amount to approximately 90°.

In order to change back from freedom from pivoting not loaded by spring force to pivoting loaded by such force, it is merely means to withdraw the stop pin 31 from the recess 29 so that accordingly free pivoting of the coupling element 28 is rendered possible in the direction of the arrow 37.

The device of the invention has been described with reference to a bracing device, in the case of which the biasing force of the spring 34 acts in the extension direction and terminal extension abutments 9; 13a and 13b are provided. As an alternative the device of the invention may furthermore readily be so designed that the spring 34 acts in the flexion direction and corresponding flexion stops are provided.

We claim:

1. A device for the reduction of a deficit in extension or bending of a distal member of a body in relation to an adjacent proximal member of the body articulatingly connected with the distal body member, comprising:

distal and proximal splints for connection with the distal and proximal body members, respectively;

a rotary joint for pivotally connecting said splints to one another, enabling relative rotation about an axis and including a spring acting between the distal and proximal splints, said spring biasing said splints for rotational movement in a predetermined direction relative to one another;

a spring force locking mechanism carried by said rotary joint and engaged with said spring for movement between a non-locking state wherein said spring biases said distal splint for movement relative to said proximal splint and a locking state wherein said spring is decoupled from the distal splint without substantial change in the bias of the spring, said spring bias being taken up by said spring force locking mechanism in said locking state, enabling the distal splint for free pivotal movement without any spring bias over a predetermined pivotal range.

2. The device according to claim 1 wherein said spring comprises a spiral spring disposed about said pivot axis, one end of said spring being operatively connected with one of said splints and another end of said spring being operatively connected with another of said splints in said non-locking state of said spring force locking mechanism.

3. The device according to claim 1 including a biasing force adjusting device operatively connected to one end of said spring for adjusting the relative position of said one spring end and another end of said spring to adjust the tension of said spring.

4. The device according to claim 3 wherein said biasing force adjusting device includes a first gear wheel rotatable about said axis and a gear wheel locking mechanism releasably locked in selected positions relative to said proximal splint, one end of said spring being secured to said gear wheel at a location near the pivot axis.

5. The device according to claim 4 wherein said gear wheel locking mechanism includes a ratchet pawl for engagement with teeth carried by said gear wheel, said pawl preventing rotation of said gear wheel in one direction of rotation and enabling said gear wheel for rotation in a direction opposite said one direction.

6. The device according to claim 5 including a second gear wheel in engagement with said first gear wheel and having a smaller diameter than said first gear wheel and constituting a transmission drive.

7. The device according to claim 4 including a second gear wheel in engagement with said first gear wheel and having a smaller diameter than said first gear wheel and constituting a transmission drive.

8. The device according to claim 1 wherein said spring force locking mechanism includes a coupling element disposed between said spring and said distal splint, said coupling element being connected with one end of said spring and engageable with said distal splint, said coupling element being urged by said spring in said non-locked state of said spring force locking mechanism into engagement with said distal splint to bias said distal splint for rotation in one direction relative to said proximal splint, said coupling element being prevented from said one direction of rotation when said spring force locking mechanism is in said locked state.

9. The device according to claim 8 wherein said coupling element comprises a disk pivotable about said pivot axis and having an entrainment member projecting on opposite sides of said disk in opposite axial directions, said entrainment member being connected on one side of said disk with said spring, said entrainment member on the opposite side of said disk being engageable with said distal splint.

10. The device according to claim 8 wherein an outer periphery of said coupling element has radially inwardly extending recesses, a stop pin carried by said proximal splint for slidable engagement into a selected one of said recesses.

11. The device according to claim 9 wherein an outer periphery of said coupling element has radially inwardly extending recesses, a stop pin carried by said proximal splint for slidable engagement into a selected one of said recesses.

\* \* \* \* \*